US006296643B1

(12) United States Patent
Hopf et al.

(10) Patent No.: US 6,296,643 B1
(45) Date of Patent: Oct. 2, 2001

(54) DEVICE FOR THE CORRECTION OF SPINAL DEFORMITIES THROUGH VERTEBRAL BODY TETHERING WITHOUT FUSION

(75) Inventors: Christoph Hopf, Albeuholz (DE); Troy Drewry; Michael C. Sherman, both of Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/421,990

(22) Filed: Oct. 20, 1999

Related U.S. Application Data

(60) Provisional application No. 60/130,909, filed on Apr. 23, 1999.

(51) Int. Cl.[7] .............................. A61B 17/68; A61B 17/70
(52) U.S. Cl. ................................................. 606/61; 606/60
(58) Field of Search .................................. 606/60, 61, 69, 606/103

(56) References Cited

U.S. PATENT DOCUMENTS

| 3,693,616 | 9/1972 | Roaf et al. | 128/69 |
|---|---|---|---|
| 4,041,939 | 8/1977 | Hall | 128/69 |
| 4,047,524 | 9/1977 | Hall | 128/69 |
| 4,078,559 | 3/1978 | Nissinen | 128/69 |
| 4,570,618 | 2/1986 | Wu | 128/69 |
| 4,573,454 | 3/1986 | Hoffman | 128/69 |
| 4,686,970 | 8/1987 | Dove et al. | 128/92 |
| 4,776,851 | 10/1988 | Bruchman et al. | 623/13 |
| 4,790,303 | * 12/1988 | Steffee | 606/61 |
| 4,870,957 | 10/1989 | Goble et al. | 128/92 |
| 4,913,134 | 4/1990 | Luque | 128/69 |
| 4,955,910 | 9/1990 | Bolesky | 623/13 |
| 4,966,600 | 10/1990 | Songer et al. | 606/74 |

(List continued on next page.)

FOREIGN PATENT DOCUMENTS

| 0 026 970 A1 | 4/1981 | (EP) . |
|---|---|---|
| 0 478 470 A1 | 1/1992 | (EP) . |
| 0 545 830 A1 | 6/1993 | (EP) . |
| 0 625 336 A2 | 11/1994 | (EP) . |
| 63-95060 | 4/1988 | (JP) . |
| WO 91/16018 | 10/1991 | (WO) . |
| WO 94/01057 | 1/1994 | (WO) . |
| WO 94/26192 | 11/1994 | (WO) . |
| WO 96/17544 | 6/1996 | (WO) . |

OTHER PUBLICATIONS

*Spinal Surgery Before and After Paul Harrington*, Spine, Jun. 15, 1998, vol. 23, No. 12.
*Atlas of Spinal Operations*, Bauer, Kerschbaumer and Poisel, Thieme Medical Publishers, Inc., 1993, pp. 160–162.
*The Use of Sublaminar Cables to Replace Luque Wires*, Songer, Spencer, Meyer, and Jayaraman, Spine, vol. 16, No. 8S, Aug. 1991, Supplement, pp. 5418–5421.
*An Anterior Approach to Scoliosis*, Dwyer, Newton and Sherwood, Clinical Orthopedics and Related Research, Jan.–Feb., 1969, No. 62.
U.S. application No. 09/421,207, Ogilvie et al., filed Oct. 20, 1999.
U.S. application No. 09/421,976, Drewry et al., filed Oct. 22, 1999.

*Primary Examiner*—Gene Mancene
*Assistant Examiner*—Michael B. Priddy
(74) *Attorney, Agent, or Firm*—Woodard, Emhardt, Naughton, Moriarty & McNett

(57) ABSTRACT

A fusionless method of treating spinal deformities in the spine of a child or young adult involves attaching a tether to vertebral bodies on the convex side of the spine. Deformities are treated by using the tether to selectively constrain growth in a portion of the convex side of the spine. One device for tethering the spine is a combination of a strand threaded through channels defined in a set of blocks attached to the vertebral bodies on the convex side of the spine.

39 Claims, 12 Drawing Sheets

U.S. PATENT DOCUMENTS

| | | | |
|---|---|---|---|
| 5,116,340 | 5/1992 | Songer et al. | 606/103 |
| 5,147,359 * | 9/1992 | Cozad et al. | 606/61 |
| 5,147,360 | 9/1992 | Dubousset | 606/61 |
| 5,306,301 | 4/1994 | Graf et al. | 623/13 |
| 5,318,566 | 6/1994 | Miller | 606/60 |
| 5,415,661 | 5/1995 | Holmes | 606/69 |
| 5,417,690 | 5/1995 | Sennett et al. | 606/61 |
| 5,423,820 | 6/1995 | Miller et al. | 606/74 |
| 5,456,722 | 10/1995 | McLeod et al. | 623/13 |
| 5,476,465 | 12/1995 | Preissman | 606/61 |
| 5,496,318 | 3/1996 | Howland et al. | 606/61 |
| 5,536,270 | 7/1996 | Songer et al. | 606/74 |
| 5,540,698 | 7/1996 | Preissman | 606/103 |
| 5,540,703 | 7/1996 | Barker, Jr. et al. | 606/139 |
| 5,545,168 | 8/1996 | Burke | 606/74 |
| 5,569,253 | 10/1996 | Farris et al. | 606/74 |
| 5,607,425 | 3/1997 | Rogozinski | 606/61 |
| 5,609,634 | 3/1997 | Voydeville | 623/17 |
| 5,628,756 | 5/1997 | Barker, Jr. et al. | 606/139 |
| 5,649,927 | 7/1997 | Kilpela et al. | 606/74 |
| 5,653,711 | 8/1997 | Hayano et al. | 606/74 |
| 5,669,917 | 9/1997 | Sauer et al. | 606/139 |
| 5,693,046 | 12/1997 | Songer et al. | 606/74 |
| 5,702,395 | 12/1997 | Hopf | 606/61 |
| 5,702,399 | 12/1997 | Kilpela et al. | 606/72 |
| 5,704,936 | 1/1998 | Mazel | 606/61 |
| 5,720,747 | 2/1998 | Burke | 606/74 |
| 5,725,582 | 3/1998 | Bevan et al. | 623/17 |
| 5,741,255 * | 4/1998 | Krag et al. | 606/61 |
| 5,741,260 | 4/1998 | Songer et al. | 606/74 |
| 5,810,815 * | 9/1998 | Morales | 606/61 |
| 5,876,403 * | 3/1999 | Shitoto | 606/61 |
| 5,908,421 | 6/1999 | Beger | 606/61 |
| 5,928,233 * | 7/1999 | Apfelbaum et al. | 606/61 |
| 6,033,429 * | 3/2000 | Magovern | 606/216 |
| 6,077,268 * | 6/2000 | Farris et al. | 606/74 |

* cited by examiner

DEVICE FOR THE CORRECTION OF SPINAL DEFORMITIES THROUGH VERTEBRAL BODY TETHERING WITHOUT FUSION

This application claims the benefit of U.S. Provisional Application No. 60/130,909, filed Apr. 23, 1999.

BACKGROUND OF THE INVENTION

Current operative methods for treating spinal deformities, particularly scoliosis, include correction of the curve by some internal fixation device, and fusion of the spine in the corrected state usually accomplished by the placement of bone graft between vertebrae. This is usually accomplished with posterior surgery, although anterior procedures are becoming more popular, as well as combinations of anterior and posterior procedures. Several instrumentation systems are available from various manufacturers to correct and stabilize the spine while fusion occurs. Among them are TSRH®, CD™, CD Hopf™, CD Horizon™, ISOLA™, Moss Miami and Synthes Universal Spine Systems. Nonoperative methods do exist and are used when applicable. These nonoperative methods include bracing and observation.

Juvenile idiopathic scoliosis occurs between the ages of 4 and 10 years. It can resolve spontaneously, respond to nonoperative therapy, or progress until fusion is required. Stapling across long bone physes has long been recognized as a predictable method of treating limb malalignment. Vertebral interbody stapling across the cartilaginous endplates and discs was attempted by Nachlas and Borden in a canine scoliosis model. Early human results in the 1950s were disappointing. Roaf reported limited successful correction of scoliosis by uninstrumented convex hemiepiphysiodesis. His study did not have a uniform patient population by skeletal maturity or scoliosis etiology.

Further shortcomings of current operative methods and devices are numerous. Patients with juvenile scoliosis who undergo curve stabilization with subcutaneous rods would be subject to multiple surgical procedures for lengthening as they grow. Anterior and/or posterior spinal fusion in the skeletally immature patient often results in loss of vertebral body height and girth. Additionally, poor self-image may occur in adolescent patients who are braced for scoliosis. Moreover, curve stabilization with bracing is only successful in approximately 75% of patients. Another problem is that some children, while not currently candidates for a definitive fusion procedure, are likely to need such a procedure in the future. These would include children less than ten years of age, small in stature, premenstrual or riser two or lower, and those not physically able to tolerate the surgery required for a definitive fusion procedure. It would be preferable to eliminate the need for that procedure altogether.

SUMMARY OF THE INVENTION

One embodiment of the invention is a device for restraining growth in a spine having a convex side and a concave side. The device comprises a strand, at least two blocks and a plurality of fasteners. Each block has a top surface, bottom surface and a first and second set of opposing side surfaces. The block is oriented on the spine so that the first set of side surfaces are located on an anterior part and a posterior part respectively of the spine. The block has a generally curved shape in a transverse direction from the anterior part to the posterior part corresponding to the antero-lateral anatomy of vertebral bodies. The bottom surface of the block is configured to contact a vertebral body. At least one fastener connects each block to at least one vertebra on the convex side of the spine. Each block has at least one channel for receiving the strand. Each block also has at least one bore extending between the top and bottom surfaces of the block. The bore receives one of the fasteners which connect the block to a vertebral body.

DESCRIPTION OF THE PREFERRED EMBODIMENT

Figure 1:
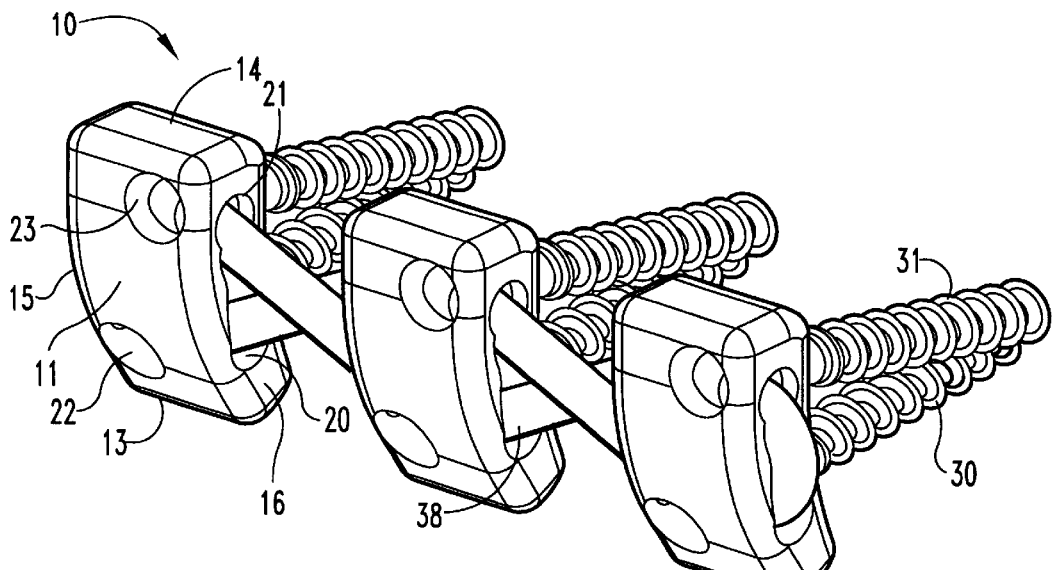
FIG. 1 is a perspective view of an embodiment of a tether of the present invention including a set of blocks and fasteners with a strand threaded through channels in the blocks.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Various devices and surgical approaches are possible to implement the underlying idea of this invention. That idea is the correction of spinal deformities, particularly scoliosis, through fusionless tethering. The correction of the deformity is achieved by attaching a tether to the vertebral bodies on the convex side of the spine. This tether will minimize or arrest growth on the convex or "long" side of the spine and allow the concave or "short" side of the spine to grow and catch up with the long side. Alternatively, fusionless tethering may treat abnormal spinal alignment by simply preventing further misalignment such as curve progression.

A wide variety of surgical approaches may be used in implementing tethering of the convex side. One approach is an open thoracotomy (standard). Another surgical approach contemplated is a minimally invasive thoracoscopic approach (endoscopic). The surgical approach may also be a combined anterior/posterior approach (standard or endoscopic). It should be understood that the invention can be practiced using other surgical approaches known to persons of ordinary skill in the art.

In any surgical approach used in practicing the invention, the tether used to selectively constrain growth will include at least one longitudinal element and one anchor with an interconnection between the longitudinal element and the anchor. In some cases the longitudinal element and the anchor may be one and the same. The following discusses generally some of the types of apparatus that may be used. Additionally, it should be understood that most, if not all, of the longitudinal elements or anchors may be manufactured from, but are not limited to, conventional implant metals, such as stainless steel or titanium. It should be further understood, and will be discussed in some detail for particular embodiments, that the longitudinal elements and anchors may take advantage of the shape memory and superelastic characteristics of shape memory materials including, for example, a shape memory alloy ("SMA") such as nickel titanium.

Several devices are contemplated for spanning the longitudinal aspect of the spine during the fusionless tethering procedure. A list of potential longitudinal elements includes, but is not limited to, staples, cables, artificial strands, rods, plates, springs, and combinations of devices from the foregoing list. Details of each individual element will be discussed briefly.

The longitudinal element may be a spinal staple formed in a variety of shapes and sizes depending on its application. Staples may act as either the longitudinal element, the anchor, or both. These staples may be manufactured from conventional implant metal, such as stainless steel or titanium. In one preferred embodiment, however, the staples are manufactured out of shape memory materials or alloys such as nickel titanium to enhance fixation. One example of such an alloy is Nitinol sold by Memry Corporation of Menlo Park, Calif. Further details of preferred use, size, and material selection for the spinal staple may be found in copending patent application U.S. Ser. No. 09/421,903 entitled "Shape Memory Alloy Staple" filed on the same day as the present application and commonly assigned to the assignee of the present application, the disclosure of which is incorporated herein by reference.

Another possible selection for the longitudinal element is cabling. Historical spinal instrumentation involved the use of cables (Dwyer) as a fixation method for spinal fusion. However, this use of cable never contemplated that a flexible cable could represent the longitudinal element in a fusionless tethering procedure.

The use of artificial or synthetic strands, much in the same way cable could be used, may potentially add additional flexibility and motion to this fusionless tethering procedure. In one preferred embodiment the artificial strand may be manufactured from a braided polymer rope. In another preferred embodiment the artificial strand will be an adjustable spinal tether. Details of various embodiments of the adjustable spinal tether may be found in provisional patent application Ser. No. 60/130,910, entitled "Adjustable Spinal Tether" filed on Apr. 23, 1999 and commonly assigned to the assignee of the present application, the disclosure of which is incorporated herein by reference. Such an artificial strand is preferably (but not necessarily) used in conjunction with a block similar or identical to various embodiments of the "Hopf blocks" disclosed in U.S. Pat. No. 5,702,395 to Hopf entitled "Spine Osteosynthesis Instrumentation for an Anterior Approach" the disclosure of which is incorporated herein by reference. It is contemplated as within the scope of the invention, however, that the artificial strand may be utilized for fusionless tethering in a variety of manners. These include, but are not limited to, being attached to or around anchors such as screws and staples. It is further contemplated as within the scope of the invention that the artificial strand may also act as both the longitudinal element and the anchor by being secured directly around the vertebrae to be tethered.

Another possible selection for the longitudinal element is a flexible rod. These could be manufactured of small diameter and/or flexible material such as a super elastic SMA. In a similar manner plates may be used as a longitudinal element. The plates can be used with or without slots allowing implants to slide. Another possible choice is a spring. Springs have been used historically in spinal instrumentation and could form the longitudinal element. Again, to reiterate, it should be understood that combinations of any or all of the above may be used as a longitudinal element when deemed appropriate.

Most of the longitudinal elements discussed above, the staples and artificial strands being possible exceptions, will need to be anchored to the vertebral bodies in order to effectively tether them. Several different anchors are contemplated.

As previously mentioned, staples can be both anchors as well as longitudinal elements since they possess the characteristics of both. These staples can be either conventional or a SMA as stated above. Also available for use in this capacity are scaled up suture anchor type products. Novel approaches using such products known in the art are available to fix to soft cancellous bone such as that found in a vertebral body. Additionally, screw down fixation plates, posts, etc. as are known to those of ordinary skill in the art, may be used as anchors.

Another potential anchor is an expandable screw. Examples include Mollie bolt type implants that are initially screwed into the vertebral body and expand through some mechanism. It is again possible to take advantage of the properties of shape memory materials to accomplish the expansion mechanism. Conventional screws and bone screws may also serve as anchors. These screws may be coated with any number of osteoinductive or osteoconductive materials to enhance fixation as desired.

The selection of the longitudinal elements and anchors from those previously discussed and others known in the art also leaves possible the selection of a wide variety of interconnections between the two. Once the anchors are in place, their connection to the longitudinal elements can be governed by a number of different parameters. They could be constrained or unconstrained connections; the anchor could be allowed to slide along the longitudinal element or articulate with it, as in the case of a ball joint, or even float within some neutral zone. Several scenarios are envisioned.

The first is constrained. This would involve constrained interconnection scenarios between all anchors and longitudinal elements. The second is unconstrained. This would involve simple connections in which no significant restrictions exist between the longitudinal element and the anchor. An example is an artificial strand band around a post, or a screw through an artificial strand ribbon.

The third scenario is ends constrained with middle elements unconstrained. In this case the construct would possess constrained interconnections between the end anchors and the longitudinal elements with unconstrained interconnections in between. These unconstrained interconnections could be either sliding situations or ball joint situations. The fourth scenario is ball joint interconnections. Ball joints represent a semiconstrained situation in which the anchor cannot slide up or down the longitudinal element, but can articulate within some spherical range of motion. It should be understood that combinations of any or all of the above may be used as appropriate in practicing the present invention.

The above disclosure deals specifically with the broad range of device concepts envisioned for fusionless tethering of deformities in order to achieve permanent correction. The specifics with regard to the method are similarly broad. A wide range of spinal deformities could be managed. The primary indications will be progressive idiopathic scoliosis with or without sagittal deformity in either infantile or juvenile patients. The preferred patient population upon which to practice the present invention is prepubescent children (before growth spurt) less than ten years old. Other patient groups upon which the present invention may be practiced include adolescents from 10–12 years old with continued growth potential. It should be understood that fusionless tethering may be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. An anterior, minimally invasive (thoracoscopic) procedure can be carried out on the convex side of the spinal curve in order to prevent continued growth on that side of the curve. As the pre-growth spurt child approaches puberty, the untethered side of the spine will grow unconstrained, ultimately eliminating the curvature of the spine in the frontal plane. It is preferable to deliver this method of treatment in a minimally invasive approach using thoracoscopic instrumentation. It is contemplated as within the scope of the invention, however, that open use of these systems may be appropriate in some cases. It is further contemplated as within the scope of the invention that the procedure may be posterior as well as anterior, or some combination of both. Finally, it should be understood that if the procedure fails to correct the curve but does, in fact, prevent further progression (which includes increase in the magnitude of the curve) it can and should be considered successful.

In one embodiment of the invention, fusionless correction of scoliosis is achieved by thoracoscopically placing shape memory alloy staples into the vertebral bodies on the convex side of the spine. The staples will span the intervertebral space and act as a tether on the spine. This tether will arrest growth on the convex ("long") side of the spine and allow the concave ("short") side of the spine to grow and catch up with the long side. Once correction is achieved, the staple may then be removed thoracoscopically if desired. The removal of the staples permits further growth of the vertebral bodies. It should be understood that the method described is equally applicable in non-endoscopic procedures. It should be further understood that the staples used may be made of a conventional implant metal such as titanium or stainless steel instead of a SMA.

Further details regarding the method of using spinal staples for the fusionless correction of scoliosis as well as details regarding the staples themselves may be found in U.S. provisional application entitled "Device and Method for the Correction of Spinal Deformities Through Vertebral Body Tethering Without Fusion" U.S. Ser. No. 60/130,909 filed Apr. 23, 1999 and U.S. application entitled "Shape Memory Alloy Staple" U.S. Ser. N0.09/421,903 filed the same day as the present application. Animal studies are currently ongoing comparing the utility of spinal staples versus a device using the blocks and strands discussed in more detail below.

Another device useful for correction of spinal deformities through fusionless tethering involves the use of blocks similar or identical to those disclosed in the above mentioned U.S. Pat. No. 5,702,395 to Hopf titled "Spine Osteosynthesis Instrumentation for an Anterior Approach" along with cabling or artificial strands. Several preferred embodiments for use as an artificial strand are disclosed in the above mentioned provisional patent application Ser. No. 60/130,910 entitled "Adjustable Spinal Tether."

Figure 2:
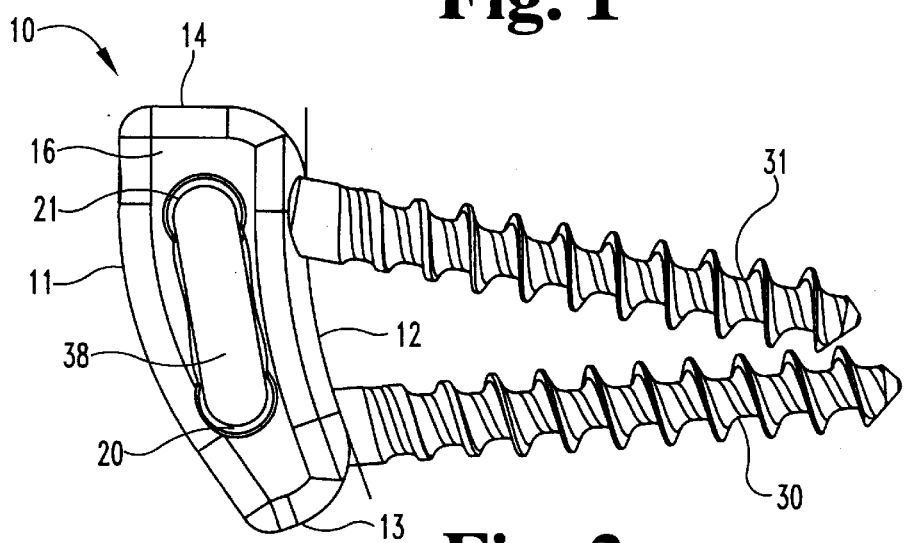
FIG. 2 is a side view of the embodiment of FIG. 1

With reference to FIGS. 1 and 2, one embodiment includes a set of three blocks with corresponding fasteners and a synthetic strand or cable threaded through channels in the blocks is shown. It should be understood that anywhere from two to greater than five blocks may be used. In one preferred embodiment the number of blocks is three. Each block 10 has a top surface 11 and a bottom surface 12 along with first and second sets of opposing side surfaces. The block 10 is oriented so that in the first set, side surfaces 13, 14 are located on an anterior and a posterior part respectively of the spine (see also FIGS. 6 and 7). The block 10 has a generally curved shape in a transverse direction from the anterior surface 13 to the posterior surface 14 corresponding to the antero-lateral anatomy of vertebral bodies. The bottom surface 12 is configured to contact a vertebral body.

Each block 10 has a second set of side surfaces 15, 16 which are oriented substantially upward and downward along the longitudinal axis $S_k$ of the spine (see FIGS. 6 and 7). The upper surface 15 and lower surface 16 of each block 10 define at least one opening or channel for receiving synthetic strand 38. In an embodiment with only one channel, the channel must either have a post or divider somewhere along its length around which the strand 38 is wrapped or else the strand 38 may be threaded through the channel and around either the top surface 11 or bottom surface 12 of each block 10. In one preferred embodiment (see FIG. 1), each block 10 has two substantially parallel channels, an anterior channel 20 and a posterior channel 21. Anterior channel 20 and posterior channel 21 extend in a direction along a line connecting upper surface 15 and lower surface 16. It is contemplated as within the scope of the invention that anterior channel 20 and posterior channel 21 may extend in different directions and/or be curved in between upper surface 15 and lower surface 16. It is further contemplated as within the scope of the invention that anterior channel 20 and posterior channel 21 may be at an angle with respect to either or both of upper surface 15 and lower surface 16. Moreover, channels 20 and 21 may both be closer to anterior surface 13 than posterior surface 14 or vice versa. Selection of various channel orientations permits configurations for the synthetic strand other than the figure eight or straight loop configuration discussed below. Also, it should be understood that the channels such as 20 and 21 may instead connect the first set of opposing side surfaces 13 and 14 or may connect some combination of the first and second sets of opposing side surfaces.

Additionally, each block 10 further defines at least one bore extending between top surface 11 and bottom surface 12. Each block 10 may have one or more bores for receiving a fastener to connect each block to a vertebral body. In one preferred embodiment block 10 has two bores, an anterior bore 22 and a posterior bore 23. It should be understood that each block 10 may have only one bore or more than two depending on the number of fasteners a surgeon wishes to use to attach each block to a vertebral body. Each bore 22, 23 extends between the top surface 11 and bottom surface 12 of block 10. Bores 22, 23 are defined in block 10 with dimensions such that each bore may receive one of the fasteners used to attach the block 10 to the vertebral body.

Figure 8A:
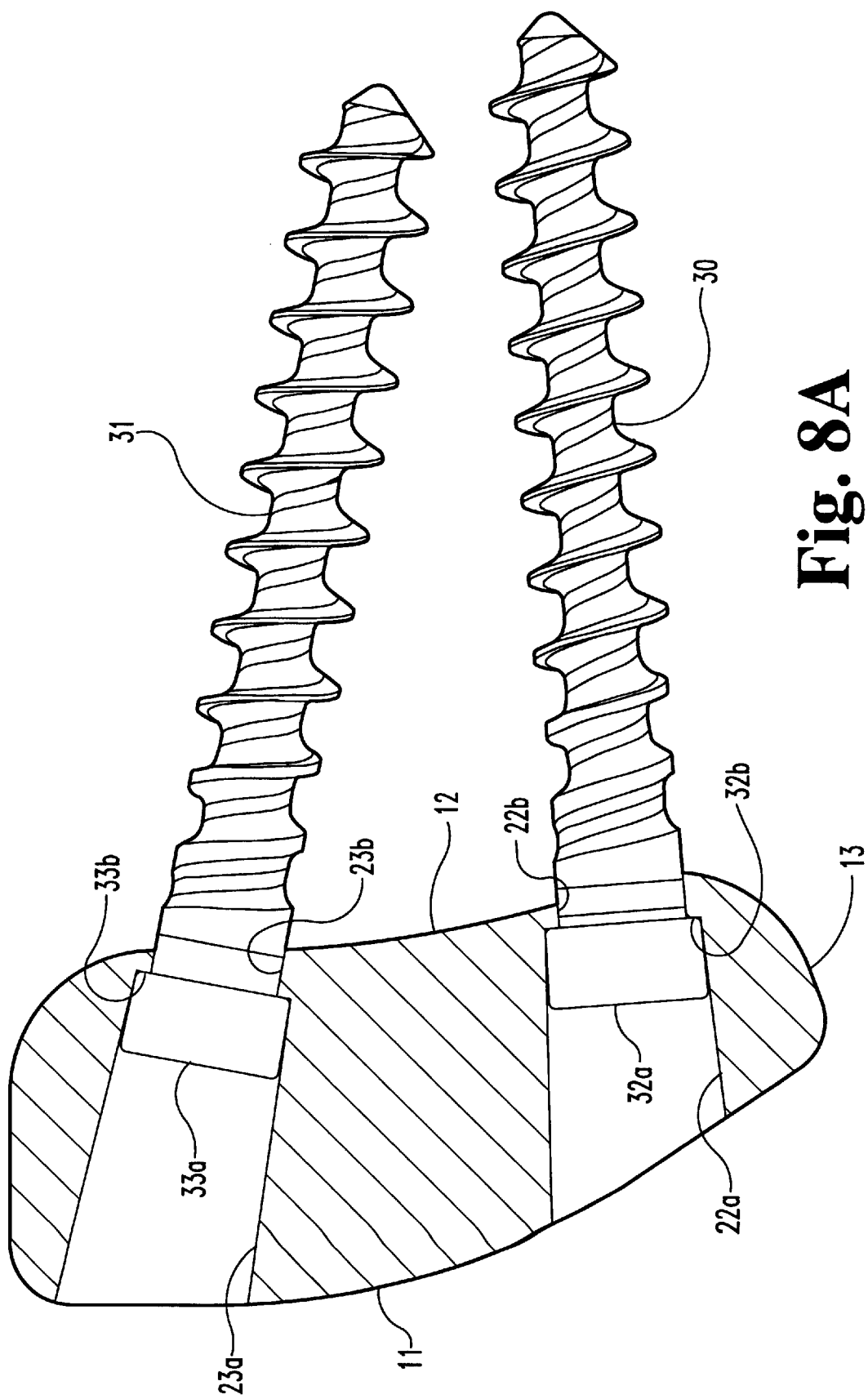
FIG. 8A is a cross-sectional view of one embodiment of the interconnection between the fasteners and the blocks.

The bottom portion of bores 22, 23 near bottom surface 12 are preferably sized to snugly receive the heads 32, 33 of fasteners 30, 31. With reference to FIG. 8A in which like elements are labeled as previously, it is seen that bore 22 has a top portion 22a and bottom portion 22b. Similarly bore 23 has a top portion 23a and a bottom portion 23b. Top portions 22a and 23a are preferably (but not necessarily) tapered for facilitating insertion of fasteners 30, 31 through bores 22, 23 respectively. The head 32 of fastener 30 has a top portion 32a with a notch therein for receiving a driving mechanism and a bottom portion 32b configured to engage the bottom portion 22b of bore 22. Similarly, the head 33 of fastener 31 has a top portion 33a with a notch therein for receiving a driving mechanism and a bottom portion 33b configured to engage the bottom portion 23b of bore 23.

Figure 8B:
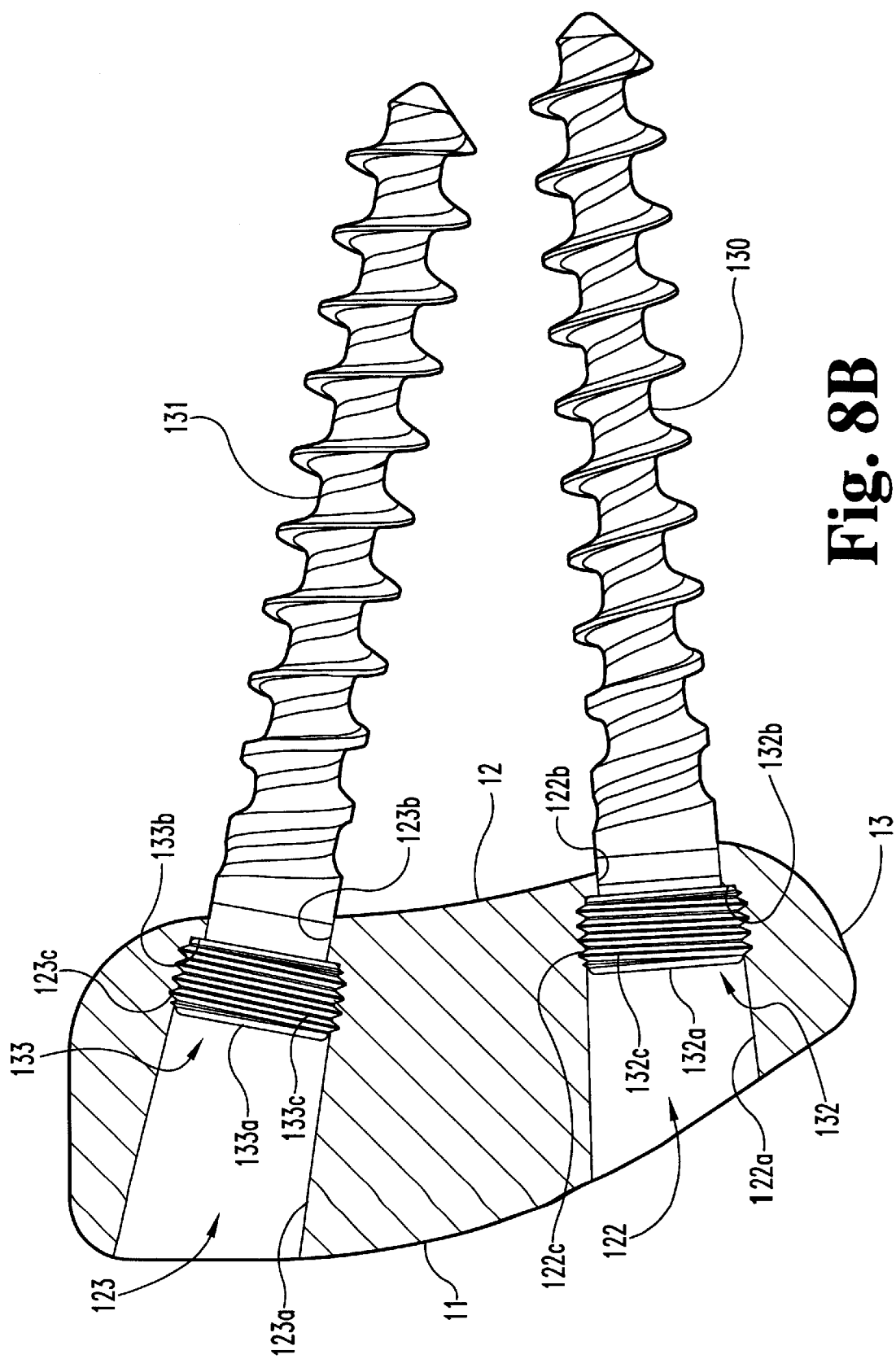
FIG. 8B is a cross-sectional view of another embodiment of the interconnection between the fasteners and the blocks having a screw back-out mechanism.

With reference to FIG. 8B, an alternative embodiment is shown with a mechanism to aid in the prevention of screw back out. With reference to FIG. 8B, in which like elements are labeled as previously, it is seen that bore 122 has a top portion 122a and bottom portion 122b. Similarly, bore 123 has a top portion 123a and a bottom portion 123b. Top portions 122a and 123a are preferably (but not necessarily) tapered for facilitating insertion of fasteners 130, 131 through bores 122, 123 respectively. The head 132 of fastener 130 has a top portion 132a with a notch therein for receiving a driving mechanism and a bottom portion 132b configured to engage the bottom portion 122b of bore 122. Similarly, the head 133 of fastener 131 has a top portion 133a with a notch therein for receiving a driving mechanism and a bottom portion 133b configured to engage the bottom portion 123b of bore 123. The head 132 of fastener 130 has external threading 132c defined thereon which engages threading 122c defined in bore 122 and aids in the prevention of screw back out. Similarly, the head 133 of fastener 131 has threading 133c defined on the head 133 which engages threading 123c defined in bore 123.

Figure 9:
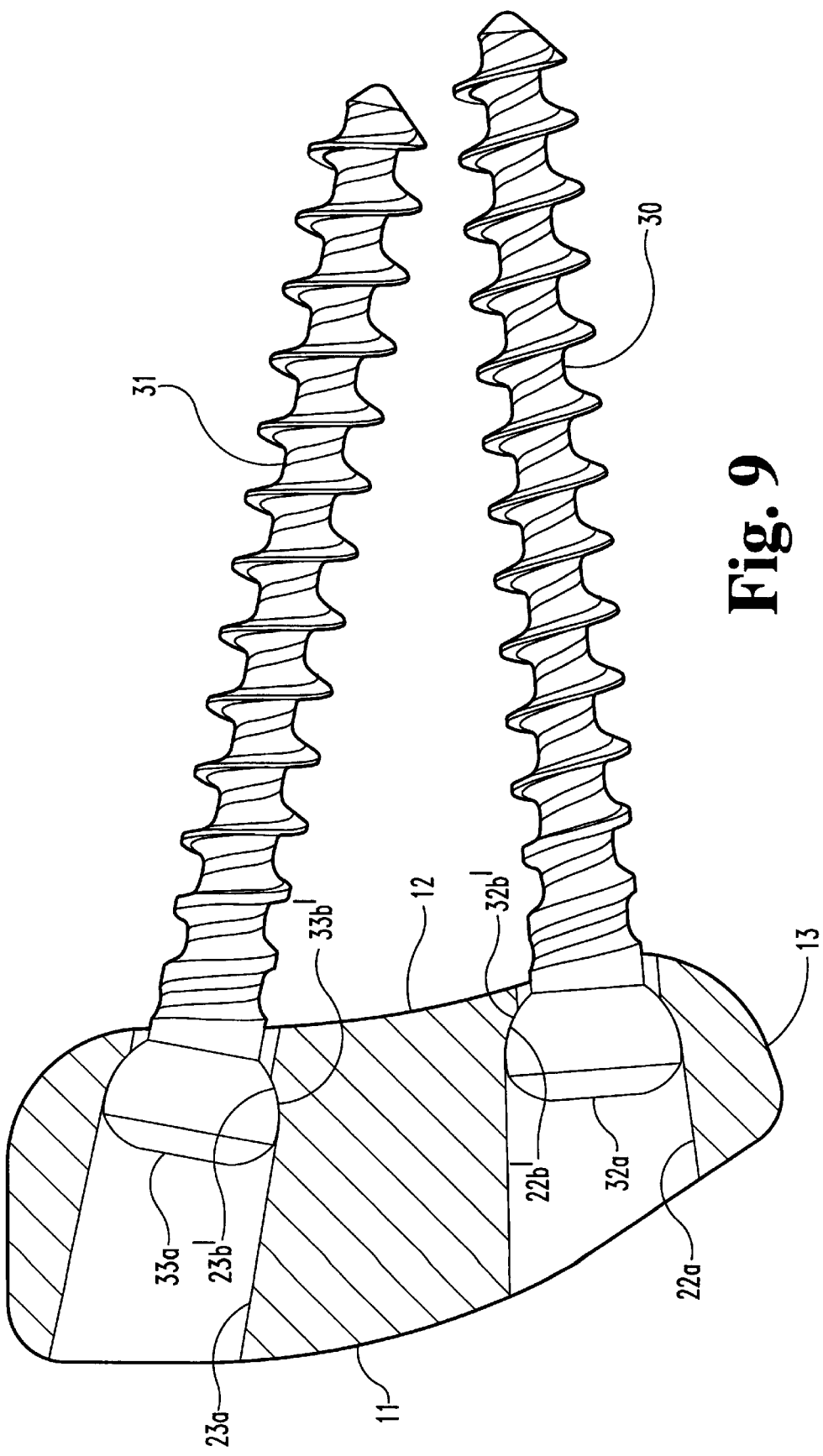
FIG. 9 is a cross-sectional view of another embodiment of the interconnection between the fasteners and the blocks.

It should be understood that bores 22, 23 may also be sized to loosely receive heads 32 and 33. The bottom portion of bores 22, 23 and heads 32, 33 may both be shaped for ball and socket interconnection allowing the pivoting or swiveling of the connecting portion of fasteners 30, 31 relative to each block 10. With reference to FIG. 9 in which like elements are labeled as previously, the bottom portions 32b', 33b' of heads 32,33 are hemispherical as are the bottom portions 22b', 23b'. Again the top portions 22a, 23a are preferably tapered to facilitate insertion of the fasteners through the bores. Alternatively, in another embodiment the bores 22, 23 and heads 32, 33 may be shaped for engagement such that the angle of the fasteners 30, 31 with respect to each other and the block 10 is substantially fixed. It should be understood that in either case, it may be desirable in some situations to use a screw back out system as described with reference to FIG. 8B or others known in the art.

In one embodiment, bore 22 intersects with channel 20 and bore 23 intersects channel 21. It should be understood, however, that the bores 22, 23 need not intersect channels 20, 21. In the embodiment where the bores 22, 23 intersect the channels 20, 21, each bore is preferably defined in such a manner that the top of heads 32, 33 of fasteners 30, 31 are not within channels 20, 21 when fasteners 30, 31 are in the bottom portion of bores 22, 23 (see FIGS. 3, 6, and 7). As a result, strand or cable 38 is unobstructed when threaded through channels 20, 21.

Figure 3:
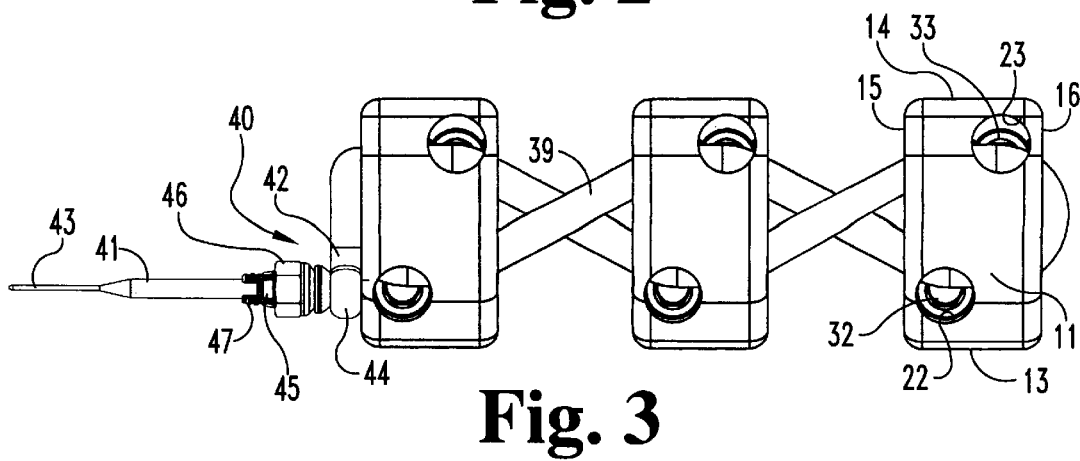
FIG. 3 is a top view of an alternative to the embodiment of FIG. 1 where the strand is an adjustable spinal tether in a figure eight configuration.
Figure 6A:
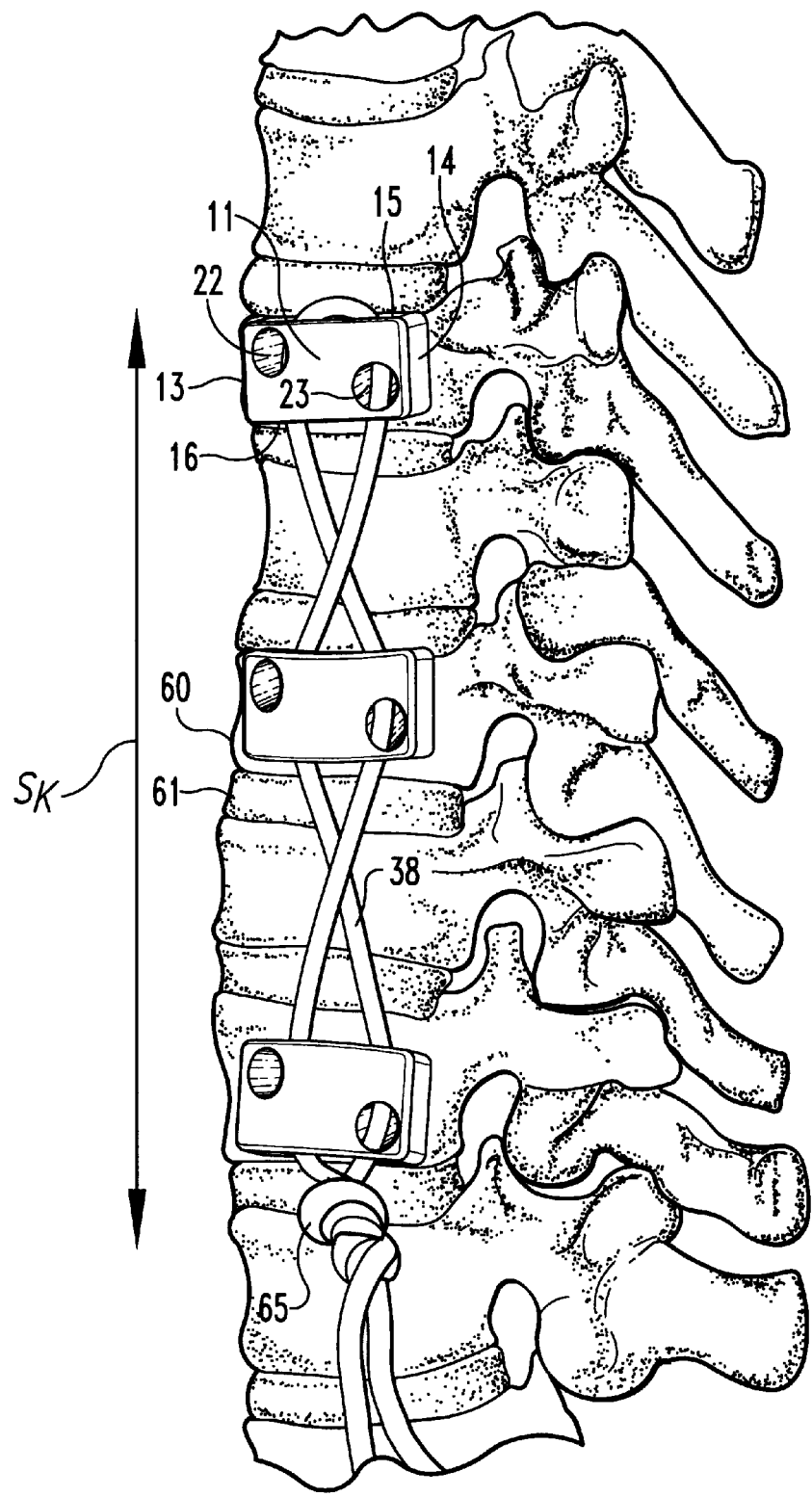
FIG. 6A is a schematic illustration of the embodiment of FIG. 1 attached to vertebral bodies on the convex side of a child's scoliotic spine.
Figure 6B:
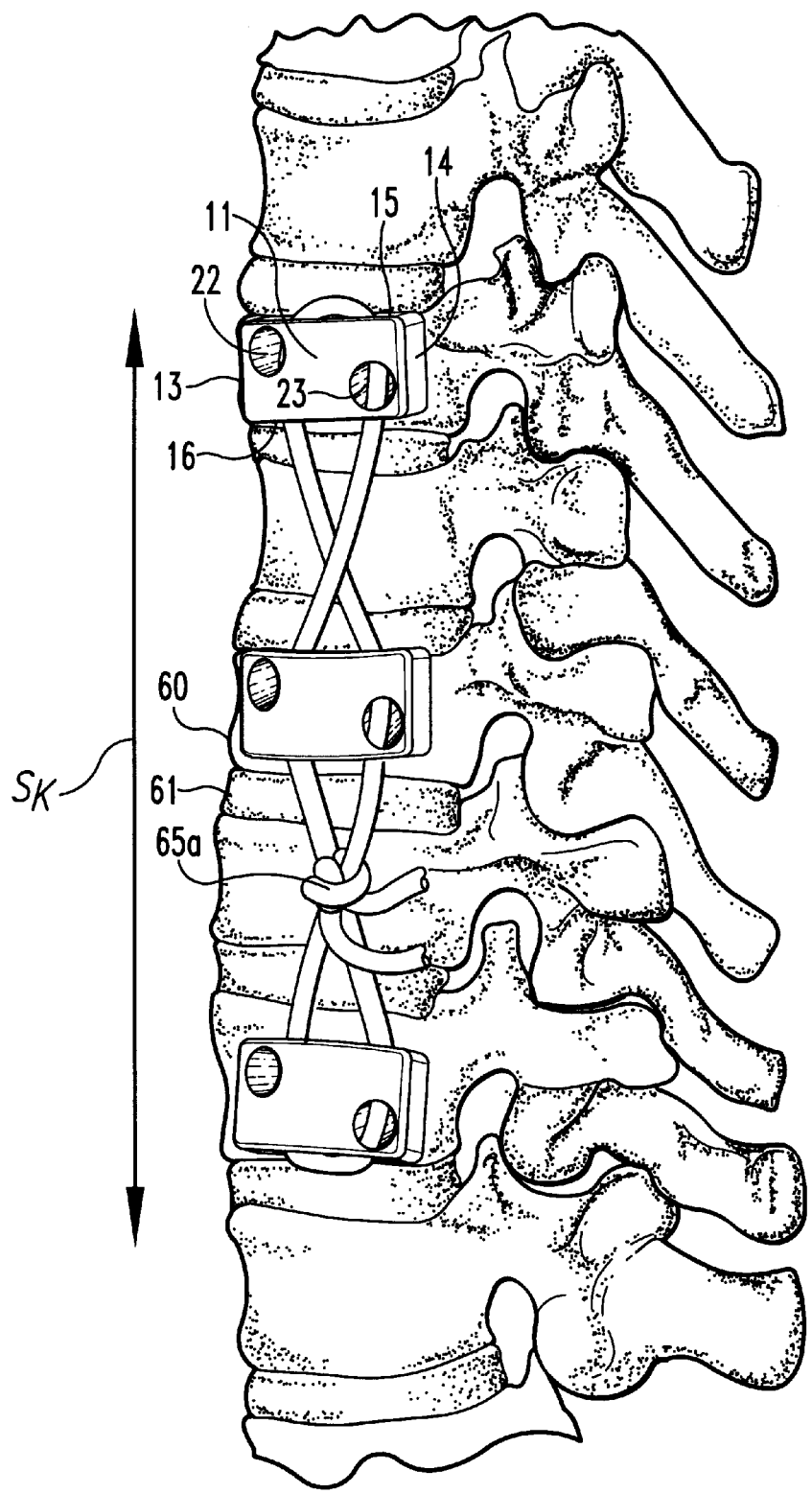
FIG. 6B is a schematic illustration of an alternative embodiment of FIG. 6A where the strand is knotted in between the blocks.
Figure 7A:
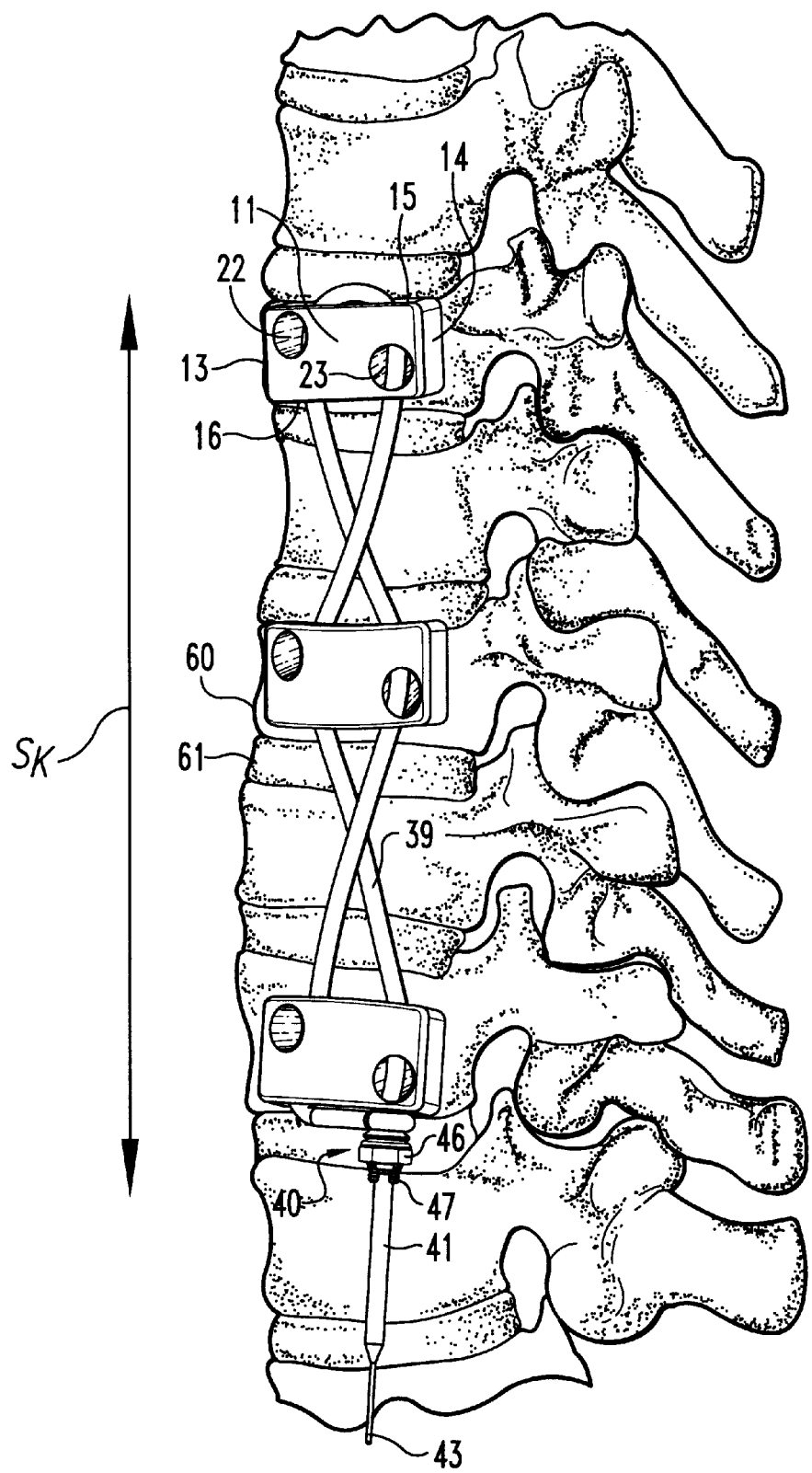
FIG. 7A is a schematic illustration of the embodiment of FIG. 3 attached to vertebral bodies on the convex side of a spine.

With reference to FIG. 1, the artificial strand 38 may be a strand with two ends tied or spliced together (see FIGS. 6A and 6B). The artificial strand 38 may be made of any suitable biocompatible material such as stainless steel or titanium or a polymer such as polyester or polyethylene. With reference to FIG. 3, another embodiment has adjustable spinal tether 40 threaded through the channels 20, 21 of blocks 10. Adjustable spinal tether 40 has a strand or cable portion 39 having a first end 41 and a second end 42. First end 41 ends in a leader 43 for ease of threading adjustable spinal tether 40 through the channels 20, 21 in blocks 10. The leader 43 may be an extrusion of first end 41 or may be otherwise affixed onto first end 41 by press fitting, adhesive, or other means known in the art. Details of various embodiments of the adjustable spinal tether construction may be found in the above mentioned patent application titled "Adjustable Spinal Tether."

Figure 4:
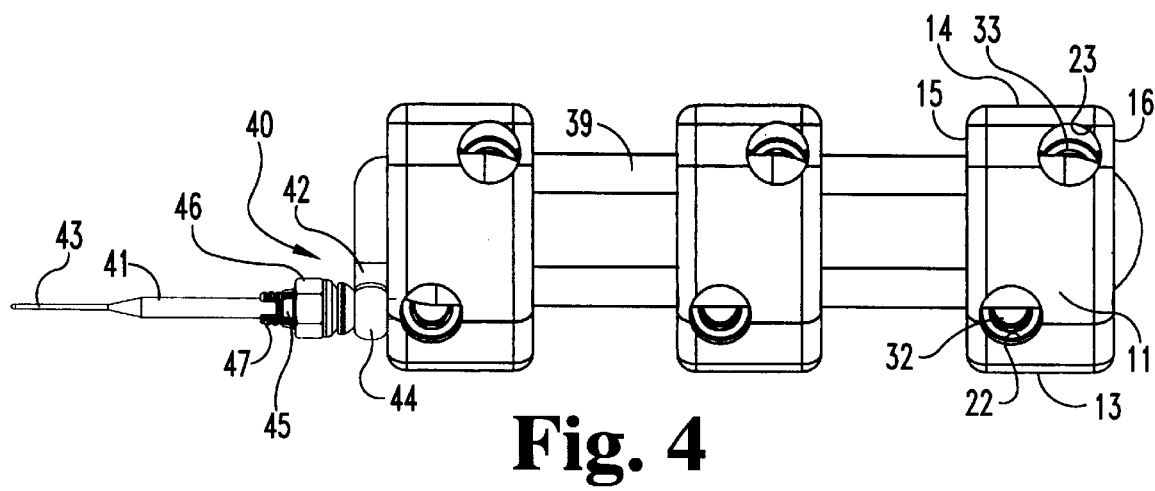
FIG. 4 is a top view of an alternative to the embodiment of FIG. 3 with the tether in a straight loop configuration.

Second end 42 may be wrapped around or otherwise attached to a grommet 44. In an alternative embodiment the adjustable spinal tether may have second end 42 looped around on itself to form an eyelet (not shown) without the need for a grommet. The leader 43 and first end 41 are threaded through grommet 44 and crimp 45 attached to the grommet 44. Crimp 45 has external threading 47 matching internal threading (not shown) on lock nut 46. Lock nut 46 is tightened down on crimp 45 to secure crimp 45 on strand or cable 39 when the appropriate length is threaded through the channels 20, 21 of blocks 10 and drawn taut. The excess length of strand 39 may then be trimmed off above crimp 45. With reference to FIGS. 1, 3 it is seen that the strand 38, 39 may be threaded through blocks 10 in a figure eight configuration. With reference to FIG. 4, in an alternative embodiment it is seen that the strand 38 may also be threaded through blocks 10 in a straight loop configuration. It should be understood that for all embodiments the strand 38 or adjustable spinal tether 40 may be threaded through the channels in the blocks 10 in either a figure eight or loop configuration or any combination of both as desired.

Figure 5:
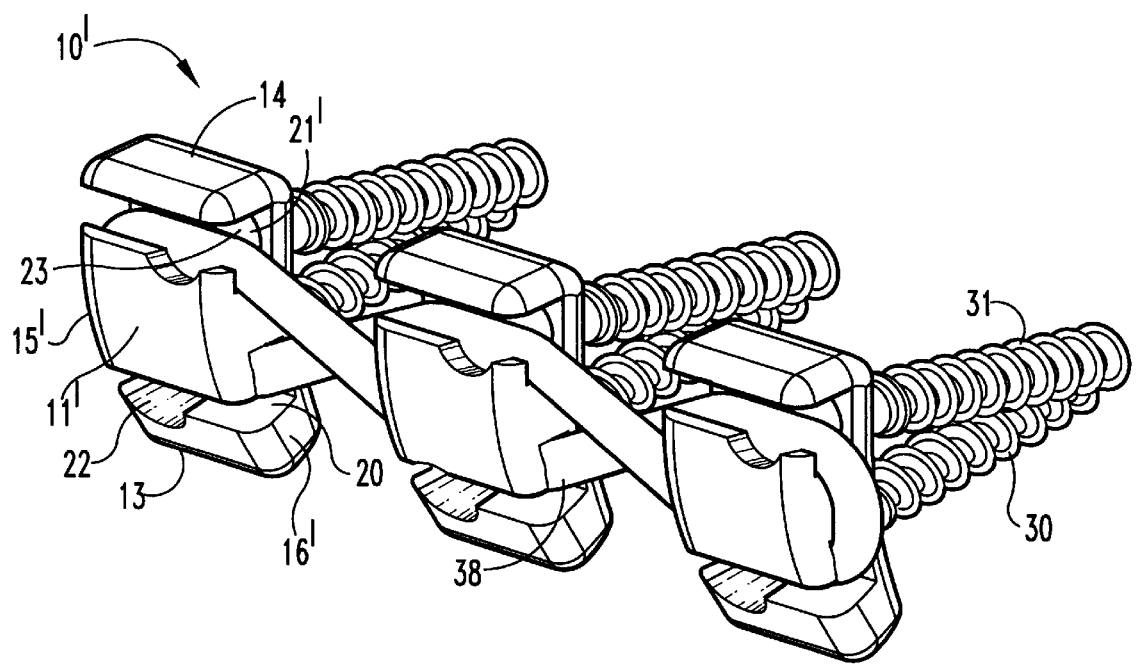
FIG. 5 is a perspective view of another embodiment in which the channels open through the top surface of the blocks.

With reference to FIG. 5, in yet another embodiment blocks 10' are shown with like elements labeled as previously. Blocks 10' have anterior channel 20' and posterior channel 21'. In this embodiment anterior channel 20' and posterior channel 21' extend between upper surface 15' and lower surface 16' as well as up through top surface 11'. Additionally, anterior channel 20' and posterior channel 21' are defined such that the portion nearer to bottom surface 12 is slightly offset from that defined in top surface 11'. The channels 20', 21' in blocks 10' permit the synthetic strand 38 to be inserted into blocks 10' through top surface 11'. Since channels 20', 21' have a slightly offset region nearer to the bottom surface 12, when synthetic strand 38 is drawn taut it is secured within the channels and will not slip out through top surface 11'.

With reference to FIG. 6A, blocks 10 are shown attached to vertebral bodies 60 with artificial strand 38 spanning intervertebral discs 61. The ends of strand 38 are shown tied together in a knot 65. It should be understood that a variety of knots may be used in place of knot 65. For example, with reference to FIG. 6B, in which like elements are labeled as previously, the knot 65a may be tied in an intermediate location between two of the vertebral blocks 11 as opposed to knot 65 as seen in FIG. 6A.

Figure 7B:
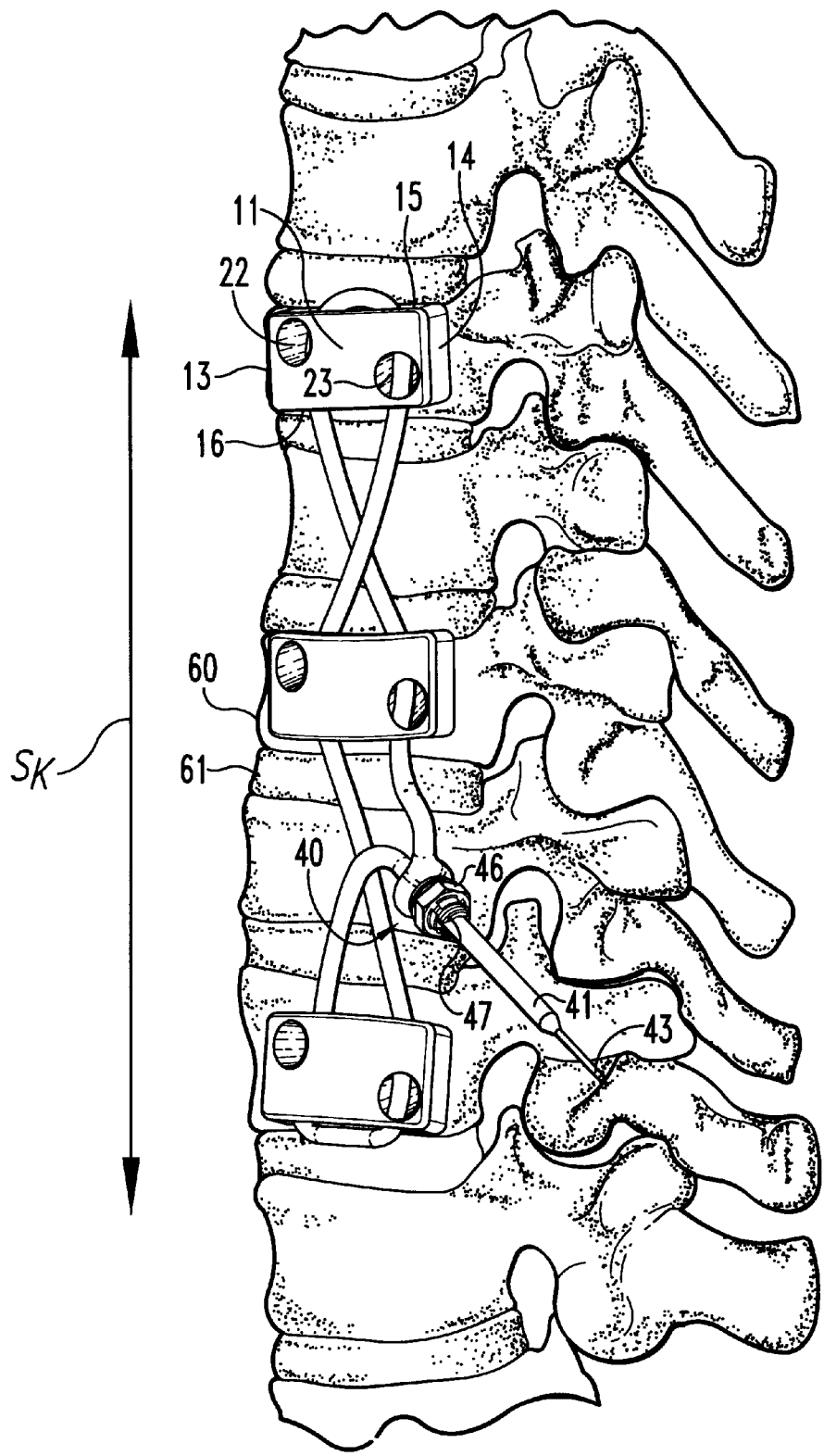
FIG. 7B is a schematic illustration of an alternative embodiment of FIG. 7A where the adjustable strand is crimped in between the blocks.

With reference to FIG. 7A, blocks 10 are again shown attached to vertebral bodies 60. In this embodiment the intervertebral discs 61 are spanned by an artificial strand 39 which is part of adjustable spinal tether 40. With reference to FIG. 7B, as in the embodiment disclosed in FIG. 6, the crimp 45 may be at an intermediate location between blocks. With reference to FIGS. 6A, 6B, 7A, and 7B, it should be noted that the arrow $S_k$ parallels the longitudinal axis of the spinal column made up of vertebral bodies and intervertebral discs.

With reference to FIGS. 10A–I, another embodiment of an anterior block for spine tethering is shown. Each block 510 has a top surface 511, a bottom surface 512, intermediate surfaces 551, 552, and first and second sets of opposing side surfaces. The block 510 is oriented so that the first set of side surfaces 513a, 513b, and 514a, 514b are located on an anterior and a posterior part respectively of the spine (similar to side surfaces 13 and 14 in FIGS. 6 and 7). The first set of side surfaces includes an upper anterior side surface 513a and a lower anterior side surface 513b and an upper posterior side surface 514a and lower posterior side surface 514b. The block 510 has a generally curved shape in a transverse direction from the lower anterior surface 513b to the lower posterior surface 514b corresponding to the antero-lateral anatomy of vertebral bodies. The bottom surface 512 is preferably (but not necessarily) configured to contact the vertebral body.

Each block 510 has a second set of side surfaces 515, 516 which are oriented to face substantially upward and downward along the longitudinal axis of the spine, similar to side surfaces 15, 16 in FIGS. 6 and 7. The upper surface 515 and lower surface 516 of each block 510 define at least one opening or channel for receiving a synthetic strand or adjustable spinal tether. In an embodiment with only one channel, the channel must either have a post or divider somewhere along its length around which the strand or adjustable spinal tether is wrapped or, alternatively, the strand or adjustable spinal tether may be threaded through the channel and around either the top surface 511 or bottom surface 512 of each block 510. In one preferred embodiment (see FIGS. 10A–I), each block 510 has two substantially parallel channels, an anterior channel 520 and a posterior channel 521. Anterior channel 520 and posterior channel 521 extend in a direction along a line connecting upper surface 515 and lower surface 516. It is contemplated as within the scope of the invention that anterior channel 520 and posterior channel 521 may extend in different directions and/or be curved in between upper surface 515 and lower surface 516. It is further contemplated as within the scope of the invention that anterior channel 520 and posterior channel 521 may be at an angle with respect to either or both of upper surface 515 and lower surface 516. Moreover, channels 520 and 521 may both be closer to anterior surface 513 than posterior surface 514 or vice versa. Selection of various channel orientations permits configurations for the synthetic strand or adjustable spinal tether other than the figure eight or straight loop configuration shown in FIGS. 3 and 4 with reference to a previously described embodiment of the block. Also, it should be understood that the channels such as 520 and 521 may instead connect the first set of opposing upper side surfaces 513a and 514a or may connect some combination of the first and second sets of opposing side surfaces.

Additionally, each block 510 further defines at least one bore extending between top surface 511 and bottom surface 512. Each block 510 may have one or more bores for receiving a fastener or connect each block to a vertebral body. In one preferred embodiment, block 510 has two bores, an anterior bore 522 and a posterior bore 523. It should be understood that each block 510 may have only one bore or more than two depending on the number of fasteners a surgeon wishes to use to attach each block to a vertebral body. Each bore 522, 523 extends between the top surface 511 and bottom surface 512 of block 510. Bores 522, 523 are defined in block 510 with dimensions such that each bore may receive one of the fasteners used to attach the block 510 to the vertebral body.

It should be understood that the bores of this embodiment of the anterior block may include features similar to those described in the previous embodiment and shown in FIGS. 8 and 9. In other words, the bores may have tapered surfaces for facilitating insertion of fasteners, may be shaped for a ball and socket interconnection, may have matching threading on the head of a fastener to prevent screw back out and the bores may be arranged in a variety of angles with respect to each other. These and other features were previously described with reference to the embodiment shown in FIGS. 8 and 9.

Figure 10D:
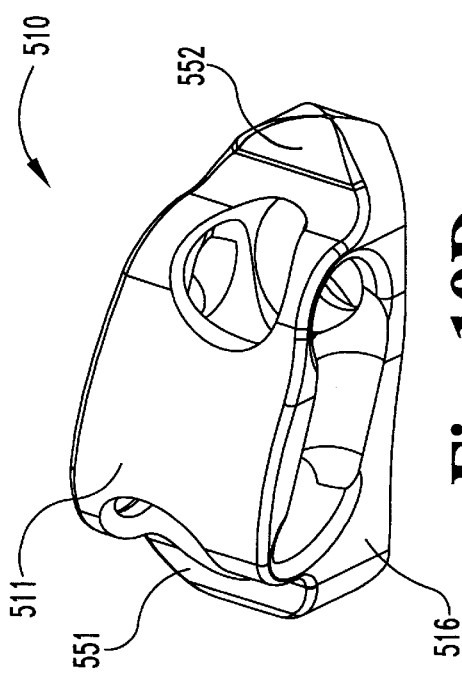
FIG. 10D is a perspective view of the embodiment of the block of FIG. 10A.
Figure 10C:
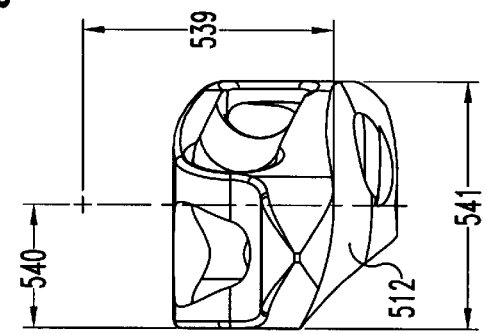
FIG. 10C is another side view of the embodiment of the block in FIG. 10A.
Figure 10B:
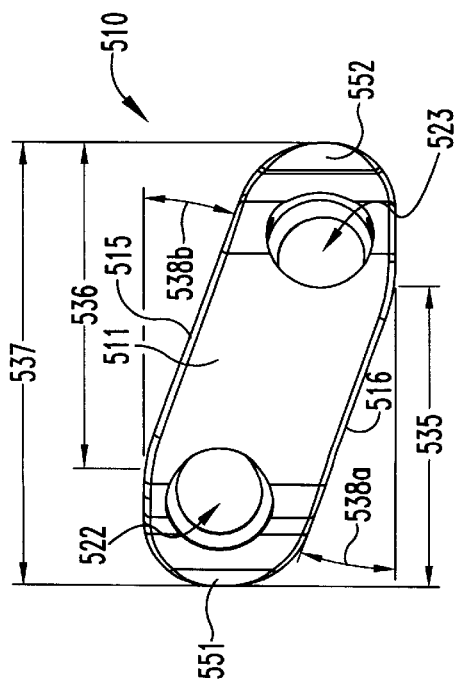
FIG. 10B is a top view of the embodiment of the block of FIG. 10A.
Figure 10A:
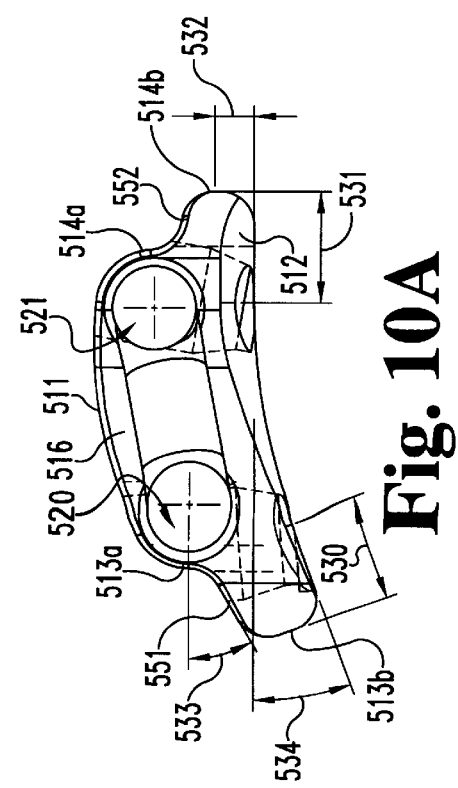
FIG. 10A is a side view of another embodiment of a block.
Figure 10E:
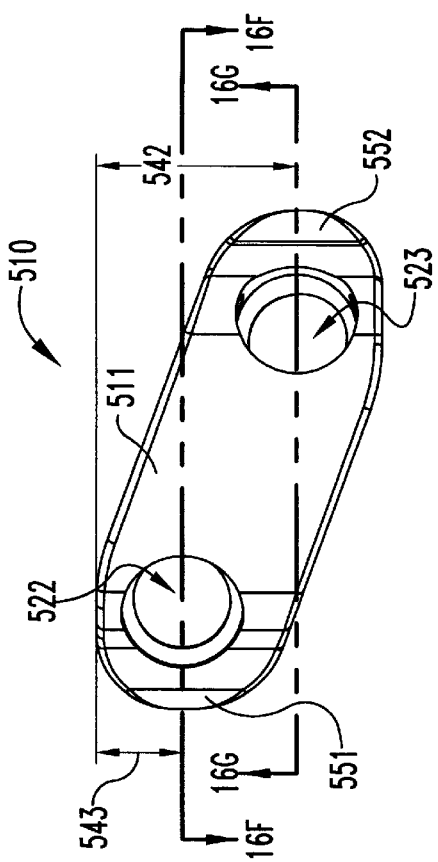
FIG. 10E is another top view of FIG. 10A illustrating further detail of the embodiment of the block.
Figure 10G:
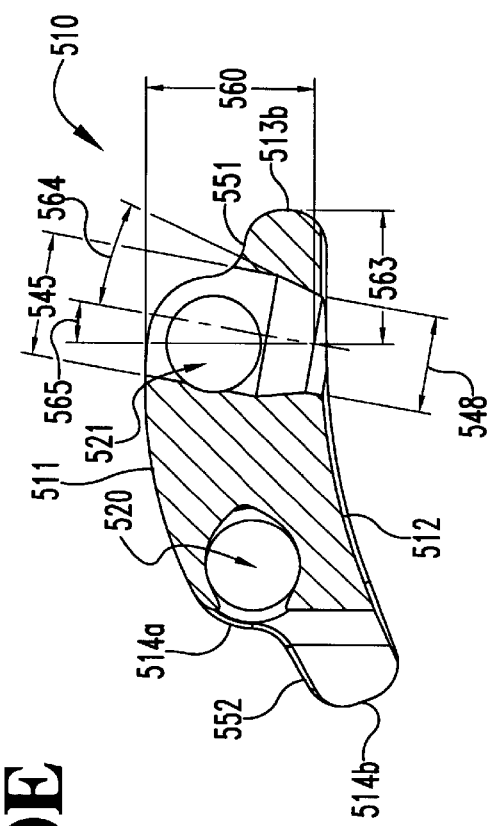
FIG. 10G is another cross-sectional view of FIG. 10E along the line 10G.
Figure 10F:
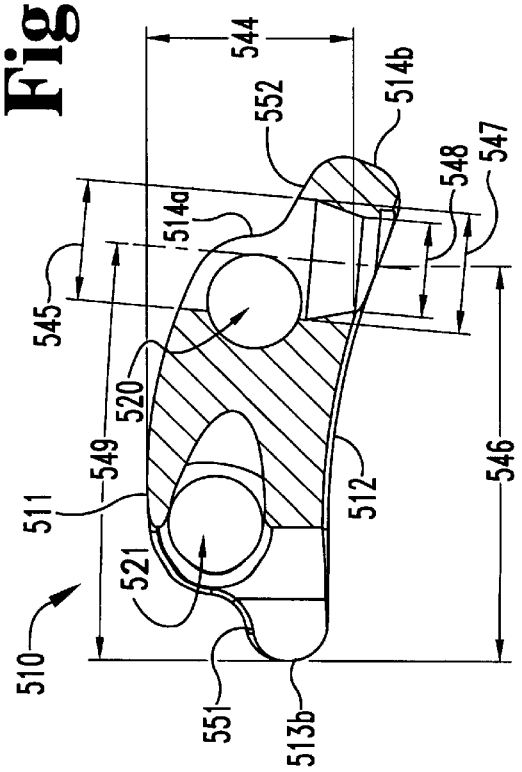
FIG. 10F is a cross-sectional view along the line 10F in FIG. 10E.
Figure 10I:
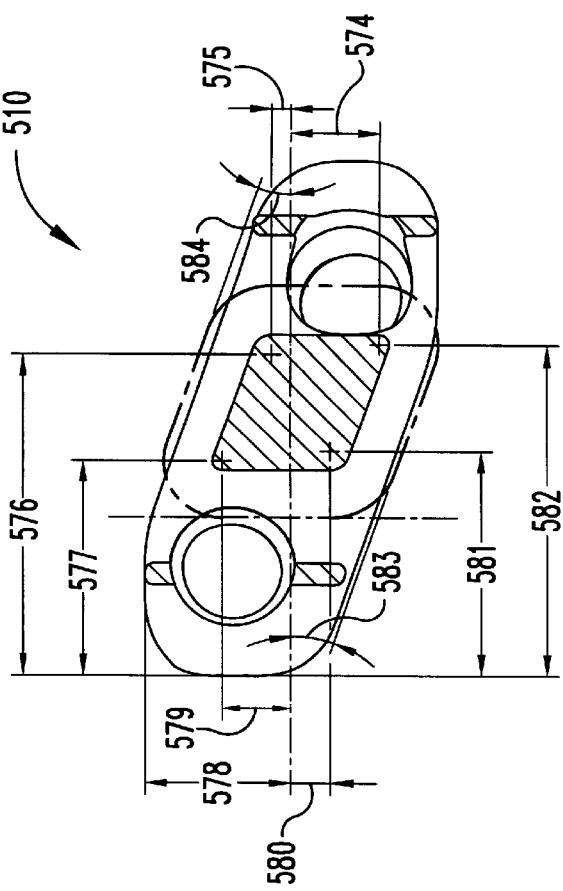
FIG. 10I is a cross-sectional view of FIG. 1OH along the lines 10I.
Figure 10H:
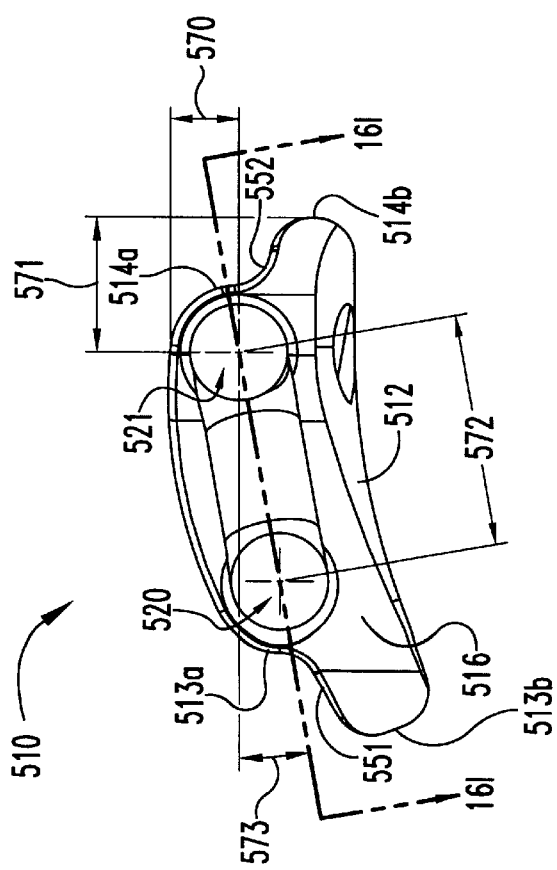
FIG. 10H is another side view of the embodiment of FIG. 10A illustrating further detail.

To better illustrate the construction of the block 510, the dimensions of one manufactured embodiment are hereafter listed. It should be understood, however, that these dimensions are exemplary and not intended to limit the scope of protection sought. The use of dimensions and tolerances other than those listed are contemplated as within the scope of the invention. With reference to FIG. 10A, length 530 is 6 mm, length 531 is 6.7 mm, length 532 is 2.33 mm, angle 533 is 30 degrees, and angle 534 is 20 degrees. With reference to FIG. 10B, length 535 is 17.82 mm, length 536 is 19.16 mm, length 537 is 26.39 mm, and angles 538a and 538b are both preferably 20 degrees. With reference to FIG. 10C, length 539 is 15 mm, length 540 is 7.5 mm, and length 541 is 15 mm. With reference to FIG. 10E, length 542 is 10.5 mm, 543 is 4.5 mm. With reference to FIG. 10F, length 544 is 10.6 mm, length 545, which defines the diameter of bore 523 at one point is 6.4 mm, length 546 is 20, length 547, which defines the diameter of the bore at one point, is 6 mm, length 548, which defines the minimum diameter of the bore is 5.05 mm, and angle 549 is five degrees. With reference to FIG. 10G, length 560 is 8.4 mm, and length 563 is 7 mm, angle 564 is 15 degrees and angle 565 is 10 degrees. With reference to FIG. 10H, length 570 is 3.1 mm, length 571 is 7 mm, length 572 is 12 mm, and angle 573 is 10 degrees. With reference to FIG. 10I, length 574 is 4.53 mm, length 575 is 1 mm, length 576 is 16.85 mm, length 577 is 11.35 mm, length 578 is 7.5 mm, length 579 is 3.53 mm, length 580 is 2 mm, length 581 is 11.85 mm, length 582 is 17.35 mm, and angles 583 and 584 are both 20 degrees. As previously mentioned, variations in these design parameters that would occur to a person of ordinary skill in the art are contemplated as within the scope of the invention.

It should be understood that the just described embodiment of a block may be used in various manners similar or identical to those shown in FIGS. 1–7 with an artificial strand or adjustable tether. The advantages of this embodiment include the reduction in the amount of volume and the amount of metal. By essentially removing portions of what was a previously rectangular cross section, this embodiment of the block has a lower profile and is less bulky.

While the invention has been illustrated and described in detail in the drawings and foregoing description, the same is to be considered illustrative and not restrictive in character, it being understood that only the preferred embodiments have been shown and described and that all changes and modifications that come within the spirit of the invention are desired to be protected.

What is claimed is:

1. A device for treating a spinal curvature without fusion, comprising:
    a plurality of bone anchors, at least one of said bone anchors adapted to engage a respective one of at least two vertebra on a convex side of the spinal curvature;
    a plurality of connectors, one of said connectors being coupled to said at least one of said bone anchors; and
    a strand extending between and interconnecting said connectors to restrain progression of the spinal curvature.

2. The device of claim 1 wherein said strand restrains growth of the spine on the convex side of the spinal curvature.

3. The device of claim 1 wherein each of said connectors defines at least one opening, said strand being disposed within each said at least one opening and made taut to interconnect said connectors.

4. The device of claim 3 wherein said at least one opening opens onto an outer surface of each of said connectors to allow said strand to be inserted transversely into said at least one opening.

5. The device of claim 3 wherein said at least one opening is a channel extending through each of said connectors; and
    wherein said strand has a first end portion and a second end portion, said strand being received within each of said channels with said first and second end portions being coupled together to form a continuous strand.

6. The device of claim 5 wherein each of said connectors defines a pair of said channels, said strand being threaded through said pair of channels in each of said connectors in a loop configuration.

7. The device of claim 5 wherein each of said connectors defines a pair of said channels, said strand being threaded through said pair of channels in each of said connectors in a figure eight configuration.

8. The device of claim 1 wherein said bone anchors are bone screws, each of said connectors defining at least one bore extending therethrough and adapted to receive a respective one of said bone screws therein to engage said connectors to said at least two vertebra.

9. The device of claim 1 wherein said strand is formed of a synthetic material.

10. The device of claim 1 wherein said strand is formed of a polymer.

11. The device of claim 10 wherein said polymer is polyethylene.

12. The device of claim 1 wherein said strand is formed of a metal.

13. The device of claim 1 wherein said strand comprises a braided rope.

14. The device of claim 1 wherein said strand comprises an adjustable spinal tether.

15. A device for treating a spinal curvature without fusion, comprising:
    a plurality of bone anchors, at least one of said bone anchors adapted to engage a respective one of at least two vertebra on a convex side of the spinal curvature;
    a plurality of blocks, one of said blocks being coupled to said at least one of said bone anchors, each of said blocks defining a bottom surface and a pair of opposite side surfaces extending from said bottom surface, one of said side surfaces being disposed adjacent an anterior portion of the spine and another of said side surfaces being disposed adjacent a posterior portion of the spine, said bottom surface defining a curved portion extending transversely between said pair of opposite side surfaces, said curved portion engaging a correspondingly shaped portion of said respective one of said at least two vertebra; and
    a strand extending between and interconnecting said connectors to restrain progression of the spinal curvature.

16. The device of claim 15 wherein said strand restrains growth of the spine on the convex side of the spinal curvature.

17. The device of claim 15 wherein said correspondingly shaped portion is the antero-lateral anatomy of said respective one of said at least two vertebra.

18. The device of claim 15 wherein each of said blocks is a single piece structure defining at least one opening, said strand being threaded through said at least one opening in each of said blocks and made taut to interconnect said connectors.

19. The device of claim 18 wherein said at least one opening and each of said opposite side surfaces are oriented in a substantially parallel relationship.

20. The device of claim 15 wherein each of said blocks defines a top surface, said at least one opening being a channel extending through each of said blocks and opening onto said top surface to allow said strand to be inserted transversely into said channel.

21. The device of claim 15 wherein said bone anchors are bone screws, each of said blocks defining a top surface and including at least one bore extending between said top and bottom surfaces, said bore being adapted to receive a respective one of said bone screws therein to engage said blocks to said at least two vertebra.

22. A device for treating a spinal curvature without fusion, comprising:
    a plurality of bone anchors, at least one of said bone anchors adapted to engage a respective one of at least two vertebra on a convex side of the spinal curvature;
    a plurality of connectors, one of said connectors being coupled to said at least one of said bone anchors, each of said connectors defining at least one opening extending therethrough; and a strand having a first end portion and a second end portion, said strand being threaded through said at least one opening in each of said connectors with said first end portion being coupled to said second end portion to form a continuous strand.

23. The device of claim 22 wherein said strand restrains progression of the spinal curvature.

24. The device of claim 22 wherein said strand constrains growth of the spine on the convex side of the spinal curvature.

25. The device of claim 22 wherein said strand is an adjustable spinal tether.

26. The device of claim 22 wherein said second end portion defines a passage, said strand being made taut by pulling said first end portion through said passage.

27. The device of claim 26 further comprising a leader affixed to said first end portion, said second end portion including a loop defining said passage, said strand being made taut by inserting said leader through said loop and pulling said first end portion through said loop.

28. The device of claim 26 wherein said first and second end portions are knotted together to form said continuous strand.

29. The device of claim 22 wherein said first and second end portions are knotted together to form said continuous strand.

30. The device of claim 22 wherein each of said connectors defines a pair of said openings extending therethrough, said strand being threaded through said pair of said openings in each of said connectors in a loop configuration.

31. The device of claim 22 wherein each of said connectors defines a pair of said openings extending therethrough, said strand being threaded through said pair of said openings in each of said connectors in a figure eight configuration.

32. The device of claim 22 wherein said bone anchors are bone screws, each of said connectors defining at least one bore extending therethrough and adapted to receive a respective one of said bone screws therein to engage said connectors to said at least two vertebra, said at least one bore intersecting said at least one opening.

33. A device for restraining growth and/or curve progression in a spine without fusion, the spine having a convex side and a concave side, comprising:
   at least two blocks, each of said blocks adapted to be coupled to a respective vertebrae on the convex side of the spine by at least one fastener, each of said blocks comprising a single piece structure and including at least one channel extending therethrough; and
   a strand threaded through said at least one channel in each of said blocks to interconnect said blocks.

34. The device of claim 33 wherein each of said blocks includes a pair of opposite side surfaces, said block being oriented so that one of said side surfaces is positioned adjacent an anterior part of the spine and another of said side surfaces is positioned adjacent a posterior part of the spine.

35. The device of claim 34 wherein each of said blocks includes a bottom surface extending transversely between said pair of opposite side surfaces, said bottom surface defining, a curved portion extending in a transverse direction and configured to engage a correspondingly shaped portion of said respective vertebrae.

36. The device of claim 35 wherein said correspondingly shaped portion is the antero-lateral anatomy of said respective vertebrae.

37. The device of claim 33 wherein each of said blocks has a generally curved shape and defines a surface configured to bear against said respective vertebrae, said surface corresponding to the antero-lateral anatomy of said respective vertebrae.

38. The device of claim 33 wherein said strand has a first end portion and a second end portion, said first and second end portions being coupled together to form a continuous strand.

39. The device of claim 38 wherein said second end portion defines a passage, said strand being made taut by pulling said first end portion through said passage, said first and second end portions being knotted together to form said continuous strand.

* * * * *